(12) United States Patent
Dieckgraefe et al.

(10) Patent No.: US 7,510,708 B2
(45) Date of Patent: Mar. 31, 2009

(54) DISRUPTION OF THE REG PATHWAY

(75) Inventors: Brian K. Dieckgraefe, Chesterfield, MO (US); Joshua R. Korzenik, Boston, MA (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 10/819,991

(22) Filed: Apr. 8, 2004

(65) Prior Publication Data

US 2004/0242526 A1 Dec. 2, 2004

Related U.S. Application Data

(60) Provisional application No. 60/462,317, filed on Apr. 14, 2003.

(51) Int. Cl.
*A61K 39/395* (2006.01)
(52) U.S. Cl. .................. 424/130.1; 424/139.1
(58) Field of Classification Search .......... None
See application file for complete search history.

(56) References Cited

U.S. PATENT DOCUMENTS

2004/0180002 A1* 9/2004 Young et al. ............... 424/1.49

FOREIGN PATENT DOCUMENTS

WO    WO 2004/003144 A2    1/2004

OTHER PUBLICATIONS

Bishnupuri et al. (2006, Gasteroenterology 130:137-149).*
Hartupee et al. (2001, Biochimica et Biophysica Acta 1518:287-293).*
Gura (1997, Science 278:1041-1042).*
Montesano et al. (1996, Intl. J. Cancer 69(3): 225-235).*
Busken et al. (2003, Digestive Disease Week Abstracts and Itinerary Planner, 2003, abstract No. 850).*
White et al, Annu Rev Med 52:125-145, 2001.*
Dieckgraefe, B.K. et al., "Expression of the regenerating gene family in inflammatory bowel disease mucosa: Reg Ialpha upregulation, processing, and antiapoptotic activity," *J. Investig. Med.* Nov. 2002; 50(6):421-34.
Macadam, RCA et al., "Death from early colorectal cancer is predicted by the presence of transcripts of the REG gene family," *British J. of Cancer* (2000) 83(2), 188-195.

* cited by examiner

*Primary Examiner*—Misook Yu
*Assistant Examiner*—Mark Halvorson
(74) *Attorney, Agent, or Firm*—Sonnenschein, Nath & Rosenthal LLP (57) ABSTRACT

Disruption of the Reg signalling pathway permits spontaneous and therapeutic induction of pro-apoptotic signals to be more effective. Disruption can be accomplished by means of antibodies, antisense, RNA interference, small molecule inhibitors, etc. These can be used in conjunction with conventional anti-neoplastic therapies. Inhibitors can be identified by assays that monitor the disruption of the binding of Reg ligands and the Reg ligand receptor.

11 Claims, 6 Drawing Sheets

SEQUENCE LISTING

```
<160> NUMBER OF SEQ ID NOS: 9

<210> SEQ ID NO 1
<211> LENGTH: 166
<212> TYPE: PRT
<213> ORGANISM: Homo sapiens

<400> SEQUENCE: 1

Met Ala Gln Thr Ser Ser Tyr Phe Met Leu Ile Ser Cys Leu Met Phe
1               5                   10                  15

Leu Ser Gln Ser Gln Gly Gln Glu Ala Gln Thr Glu Leu Pro Gln Ala
            20                  25                  30

Arg Ile Ser Cys Pro Glu Gly Thr Asn Ala Tyr Arg Ser Tyr Cys Tyr
        35                  40                  45

Tyr Phe Asn Glu Asp Arg Glu Thr Trp Val Asp Ala Asp Leu Tyr Cys
    50                  55                  60

Gln Asn Met Asn Ser Gly Asn Leu Val Ser Val Leu Thr Gln Ala Glu
65                  70                  75                  80

Gly Ala Phe Val Ala Ser Leu Ile Lys Glu Ser Gly Thr Asp Asp Phe
                85                  90                  95

Asn Val Trp Ile Gly Leu His Asp Pro Lys Lys Asn Arg Arg Trp His
            100                 105                 110

Trp Ser Ser Gly Ser Leu Val Ser Tyr Lys Ser Trp Gly Ile Gly Ala
        115                 120                 125

Pro Ser Ser Val Asn Pro Gly Tyr Cys Val Ser Leu Thr Ser Ser Thr
    130                 135                 140

Gly Phe Gln Lys Trp Lys Asp Val Pro Cys Glu Asp Lys Phe Ser Phe
145                 150                 155                 160

Val Cys Lys Phe Lys Asn
                165

<210> SEQ ID NO 2
<211> LENGTH: 166
<212> TYPE: PRT
<213> ORGANISM: Homo sapiens

<400> SEQUENCE: 2

Met Ala Gln Thr Asn Ser Phe Phe Met Leu Ile Ser Ser Leu Met Phe
1               5                   10                  15
```

Leu Ser Leu Ser Gln Gly Gln Glu Ser Gln Thr Glu Leu Pro Asn Pro
            20                  25                  30

Arg Ile Ser Cys Pro Glu Gly Thr Asn Ala Tyr Arg Ser Tyr Cys Tyr
            35                  40                  45

Tyr Phe Asn Glu Asp Pro Glu Thr Trp Val Asp Ala Asp Leu Tyr Cys
50                  55                  60

Gln Asn Met Asn Ser Gly Asn Leu Val Ser Val Leu Thr Gln Ala Glu
65                  70                  75                  80

Gly Ala Phe Val Ala Ser Leu Ile Lys Glu Ser Ser Thr Asp Asp Ser
                85                  90                  95

Asn Val Trp Ile Gly Leu His Asp Pro Lys Lys Asn Arg Arg Trp His
                100                 105                 110

Trp Ser Ser Gly Ser Leu Val Ser Tyr Lys Ser Trp Asp Thr Gly Ser
            115                 120                 125

Pro Ser Ser Ala Asn Ala Gly Tyr Cys Ala Ser Leu Thr Ser Cys Ser
            130                 135                 140

Gly Phe Lys Lys Trp Lys Asp Glu Ser Cys Glu Lys Lys Phe Ser Phe
145                 150                 155                 160

Val Cys Lys Phe Lys Asn
                165

<210> SEQ ID NO 3
<211> LENGTH: 175
<212> TYPE: PRT
<213> ORGANISM: Homo sapiens

<400> SEQUENCE: 3

Met Leu Pro Pro Met Ala Leu Pro Ser Val Ser Trp Met Leu Leu Ser
1               5                   10                  15

Cys Leu Met Leu Leu Ser Gln Val Gln Gly Glu Glu Pro Gln Arg Glu
            20                  25                  30

Leu Pro Ser Ala Arg Ile Arg Cys Pro Lys Gly Ser Lys Ala Tyr Gly
            35                  40                  45

Ser His Cys Tyr Ala Leu Phe Leu Ser Pro Lys Ser Trp Thr Asp Ala
        50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
                100                 105                 110

Thr Glu Pro Asn Gly Glu Gly Trp Glu Trp Ser Ser Ser Asp Val Met
            115                 120                 125

Asn Tyr Phe Ala Trp Glu Arg Asn Pro Ser Thr Ile Ser Ser Pro Gly
            130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Phe Thr Asp
                165                 170                 175

<210> SEQ ID NO 4
<211> LENGTH: 158
<212> TYPE: PRT
<213> ORGANISM: Homo sapiens

<400> SEQUENCE: 4

Met Ala Ser Arg Ser Met Arg Leu Leu Leu Leu Ser Cys Leu Ala
1               5                   10                  15

Lys Thr Gly Val Leu Gly Asp Ile Ile Met Arg Pro Ser Cys Ala Pro
            20                  25                  30

Gly Trp Phe Tyr His Lys Ser Asn Cys Tyr Gly Tyr Phe Arg Lys Leu
            35                  40                  45

Arg Asn Trp Ser Asp Ala Glu Leu Glu Cys Gln Ser Tyr Gly Asn Gly
50                  55                  60

Ala His Leu Ala Ser Ile Leu Ser Leu Lys Glu Ala Ser Thr Ile Ala
65                  70                  75                  80

Glu Tyr Ile Ser Gly Tyr Gln Arg Ser Gln Pro Ile Trp Ile Gly Leu
                85                  90                  95

His Asp Pro Gln Lys Arg Gln Gln Trp Gln Trp Ile Asp Gly Ala Met
            100                 105                 110

Tyr Leu Tyr Arg Ser Trp Ser Gly Lys Ser Met Gly Gly Asn Lys His
            115                 120                 125

Cys Ala Glu Met Ser Ser Asn Asn Asn Phe Leu Thr Trp Ser Ser Asn
130                 135                 140

Glu Cys Asn Lys Arg Gln His Phe Leu Cys Lys Tyr Arg Pro
145                 150                 155

<210> SEQ ID NO 5
<211> LENGTH: 10
<212> TYPE: PRT
<213> ORGANISM: Homo sapiens

<400> SEQUENCE: 5

Glu Phe Asp Ile Ile Met Arg Pro Ser Cys
1               5                   10

<210> SEQ ID NO 6
<211> LENGTH: 7
<212> TYPE: PRT
<213> ORGANISM: Homo sapiens

<400> SEQUENCE: 6

Glu Phe Asp Ile Ile Met Arg
1               5

<210> SEQ ID NO 7
<211> LENGTH: 30
<212> TYPE: DNA
<213> ORGANISM: Homo sapiens

<400> SEQUENCE: 7
ggaattcgat atcatcatga gacccagctg                                    30

<210> SEQ ID NO 8
<211> LENGTH: 31
<212> TYPE: DNA
<213> ORGANISM: Homo sapiens

<400> SEQUENCE: 8
ctaactcctg cacagccccg tcctctagag g                                  31

<210> SEQ ID NO 9
<211> LENGTH: 8
<212> TYPE: PRT
<213> ORGANISM: Homo sapiens

```
<400> SEQUENCE: 9

Asp Ile Ile Met Arg Pro Ser Cys
 1               5
```

DISRUPTION OF THE REG PATHWAY

This application claims the benefit of provisional application Ser. No. 60/462,317 filed Apr. 14, 2003, the contents of which are expressly incorporated herein.

This invention was made using funds from the United States government (grant no. 1R01 DK60106-01A1). The U.S. government therefore retains certain rights in the invention.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The invention relates to the field of cancer therapeutics and drug development. In particular it relates to cancers that express proteins of the REG pathway.

BACKGROUND OF THE INVENTION

Antitumor drugs and radiation therapy work, to a significant degree, by activation of tumor cell apoptosis (Reed, J C. et al. J. Cell. Biochem 60:23-32, 1996). Therapeutic efficacy is therefore dependent on inherent mechanisms that regulate susceptibility to apoptosis. Apoptosis is regulated by at least two pathways; mitochondrial pathways and membrane death receptors (Green D R., Science 281:1309-12, 1998, Ashkenazi A., Curr Opin Cell Bio 11:225-260, 1999, Gross, A. et al. Genes Dev 13:1899-911, 1999). Mitochondrial release of cytochrome c into the cytosol activates procaspase-9 with resulting activation of downstream effector caspases and cellular apoptosis. Activated caspases are responsible for the proteolytic events important in mediation of apoptosis. Several antiapoptotic proteins, including Bcl-2, Bcl-XL, or Bcl-W, inhibit mitochondrial release of cytochrome c and prevent alteration of the megachannel (Green D R., Science 281: 1309-12, 1998, Li, P., Cell 91:479-89, 1997, Yang, J., Science 275:1129-32, 1997, Tsujimoto, Y., FEBS Lett 466:6-10, 2000).

Thus anti-apoptotic proteins can stabilize mitochondrial membrane integrity, prevent cytochrome release, and block apoptosis. These molecular events contribute to the intrinsic tumor resistance to cytotoxic drugs and radiation (Sun Y., Cancer Res 62:6323-28, 2002, Violette, S., Int. J. Cancer 98:498-504, 2002, Amundson, SA., Cancer Res 60:6101-10, 2000). In vivo studies have confirmed these concepts, showing that high Bcl-2, and/or Bcl-XL are predictive of a poor prognosis in patients with colon cancer (Ogura, E., Oncol Rep 6:365-9, 1999, and Maurer Calif., Dig Dis Sci 43:2641-8, 1998). Bcl-2-mediated inhibition of in vivo apoptosis may also prevent immunogenicity of tumors, thus contributing to a progressive, metastatic and lethal phenotype of otherwise regressive clonal variants that arise during tumor growth (Bonnotte, B., J of Immuno. 161:1433-38, 1998). Thus one component of the persistence/resistance of tumor cells with increased Bcl-2 expression may reflect a reduced capacity to induce a host immune response.

Bcl-2 can be upregulated after treatment with prostaglandins (PGE2) in tumor cells (Sheng, H., Cancer Res 58:362-366, 1998). COX-2 mediated production of PGE2 may contribute to tumor resistance, in part, by regulating antiapoptotic gene expression. Yet, Bcl-2 levels are maintained in cells treated with NSAIDs, suggesting that up-regulation of Bcl-2 can occur independently of PGE2 (Sun Y., Cancer Res 62:6323-28, 2002). Increased expression of Bcl-2, and Bcl-XL are noted in colorectal tumors compared with histologically normal mucosa (Sinicrope F A., Cancer Res 55:237-41, 1995). Thus factors that are responsible for the up-regulation of Bcl-2 family genes in tumors appear to represent a promising and yet unexplored therapeutic avenue.

One kinase responsible for protection against apoptosis in tumor cells may be Akt/protein kinase B. Akt, also referred to as Rac regulate the balance between survival and apoptosis by several mechanisms. Akt is activated by a variety of growth factors (Burgering B T., et al. Nature 376:599-602, 1995, Franke T F., et al. Cell 81:727-36, 1995) and acts in a LY294002 (inhibitor of PI3K) and Wortmannin-sensitive pathway. Akt is activated by phospholipid binding and phosphorylation localized to at least two sites (Thr308 and Ser473). Activated Akt inactivates by phosphorylation several targets, including caspase 9, Bad, GSK3, and members of the forkhead transcription factor family. Akt overexpression has been shown to be a critical and early event during sporadic colon carcinogenesis (Roy, H K., et al Carcinogenesis 23:201-5, 2002). Furthermore, phosphorylation of Akt is required for suppression of apoptosis and tumor progression of human colorectal carcinoma (Itoh N., et al Cancer 94:3127-34, 2002). Itoh showed that expression of phosphorylated Akt (Ser473) by immunohistochemistry was correlated with depth of invasion, lymph node metastasis, and advanced tumor stage in human colorectal. Correlation with Bcl-2 expression nearly reached statistical significance as well. In this study, increased phosphorylated Akt expression was also directly correlated with an increasing growth index and a decreased apoptotic index in human tumor tissue resection specimens. Direct inhibition of the Akt pathway, such as with LY294002, may have considerable toxicity given the potential physiologic role in normal cell senescence and differentiation in the colorectal mucosa (Alessi D R., et al. Curr Biol 7:261-69, 1997, Klippel A., et al Mol Cell Biol 17:338-44, 1997) as well as other tissues. This makes determination and selective targeting of relevant tumor upstream activators of the Akt pathway theoretically preferable.

Figure 1:
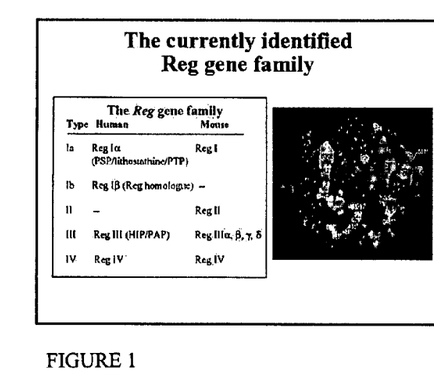
FIG. 1 show the Reg gene family members in human and mouse.

The human Reg gene family of ligands consists of four secreted and structurally unique protein that share sequence similarity with the carbohydrate-binding domain of C-type lectins (FIG. 1). The initial cDNA in this gene family was named Reg for its role in islet of Langerhans regeneration following partial pancreatectomy (now known as Reg I$\alpha$). Additional members of the human Reg gene family are regenerating gene homologue (Reg I$\beta$) and pancreatitis-associated protein (Reg III). All are constitutively expressed in the normal proximal gastrointestinal tract. While the function of this gene family is poorly understood, recent data has suggested that Reg family members may function as tissue mitogens. Reg I$\alpha$ is mitogenic for gastric mucosal cells (Fukui H., et al. Gastro 115:1483-93, 1998), and pancreatic ductal and beta cells (Zenilman, Me., et al. Gastroenterology 110:1208-14, 1996, Zenilman, Me., et al. Pancreas 17:256-61, 1998, Watanabe, T., PNAS 91:3589-92, 1994). The serum concentration of Reg I$\alpha$ is significantly increased in many gastrointestinal malignancies, including gastric and pancreatic adenocarcinoma (Satomura, Y., et al. J Gastroenterology 30:643-50, 1995). For patients with early stage colonic adenocarcinoma undergoing surgical resection, Reg I$\alpha$ mRNA expression alone or co-expression of Reg I$\alpha$ and Reg III mRNA by the carcinoma had an adverse affect on disease free survival that was independent of tumor stage or site (Macadam, RCA., et al British J Cancer 83:188-95, 2000).

Figure 2:
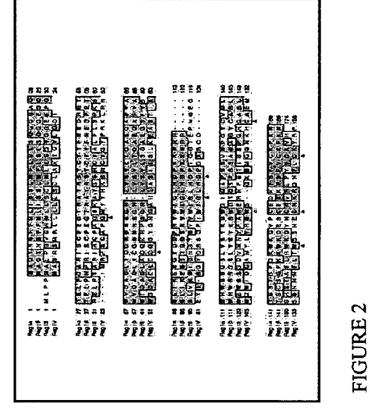
FIG. 2 shows a comparison of the amino acid sequences of the Reg gene family members. (SEQ ID NO: 1-4).

We recently identified a novel member of this gene family, Reg IV, which has significant constitutive expression in the distal gastrointestinal tract (Hartupee J C., et al BBA 1518: 287-93, 2001). We showed by molecular modeling, that the Reg IV protein showed maintenance of the conserved contact surface residues that cluster on a single face of the 3-dimensional molecule present in all other members of the Reg gene family (FIGS. 1 and 2). This suggests that Reg proteins may share similar physiologic actions. Reg IV is of considerable interest because of its possible role, along with other members of the Reg gene family in the pathogenesis of colorectal adenocarcinoma. Reg IV is overexpressed by a majority of colorectal adenocarcimonas. By differential display, Reg IV was among several genes with increased mRNA expression in several colon cancer cell lines selected for increased in vitro resistance to a cancer chemotherapeutic agent, 5-FU (Violette S et al, Int J. Cancer 103:185-193).

Expression of many genes is increased or decreased in gastrointestinal malignancy as compared with the normal gastrointestinal mucosa. This correlation does not provide a causative association (e.g., apoptosis resistance or malignant phenotype). In fact most differentially regulated genes will not serve an integral role in the malignancy process or offer a currently recognizable therapeutic intervention. There is a need in the art to identify genes that do serve an integral role in the malignancy process and which will offer therapeutic interventions.

BRIEF SUMMARY OF THE INVENTION

In a first embodiment of the invention an antisense construct is delivered to a tumor cell. The construct comprises at least 15 nucleotides of the complement of a rat, mouse, or human Reg gene family cDNA selected from the group consisting of RegIα, RegIβ, RegIII, RegIV, and EXTL3. As a result of the delivery, the tumor cell expresses an mRNA molecule which is complementary to native mRNA of the Reg gene.

In a second embodiment of the invention an RNA interference construct is delivered to a tumor cell. The construct comprises at least 19 nucleotides of a rat, mouse, or human Reg gene family cDNA selected from the group consisting of RegIα, RegIβ, RegIII, RegIV, and EXTL3. As a result of the delivery, the tumor cell expresses a double stranded RNA molecule which is complementary to native mRNA of the Reg family gene.

According to a third embodiment of the invention a method is provided for causing cleavage of a Reg gene mRNA produced by a tumor cell. A siRNA is delivered to the tumor cell. The siRNA comprises 19 to 21 bp duplexes of a rat, mouse, or human Reg gene family RNA selected from the group consisting of RegIα, RegIβ, RegIII, RegIV, and EXTL3. The siRNA has 2 nt 3' overhangs.

According to a fourth embodiment of the invention a method is provided for identifying a test substance that inhibits binding of a Reg protein to the EXTL3 protein. A rat, mouse, or human EXTL3 protein is contacted with a rat, mouse, or human Reg protein in the presence and in the absence of a test substance. The Reg protein is selected from the group consisting of RegIα, RegIβ, RegIII, and RegIV. Binding of the Reg protein to the EXTL3 protein is determined in the presence and in the absence of a test substance. A test substance which inhibits binding of the Reg protein to the EXTL3 protein is identified.

According to a fifth embodiment of the invention an inhibitor is delivered to a tumor cell. The inhibitor inhibits the binding of a rat, mouse, or human EXTL3 protein to a rat, mouse, or human Reg protein selected from the group consisting of RegIα, RegIβ, RegIII, and RegIV. Resistance to apoptosis by the tumor cell is thereby reduced.

According to a sixth embodiment of the invention an antibody is delivered to a tumor cell. The antibody specifically binds to a rat, mouse, or human Reg family protein selected from the group consisting of RegIα, RegIβ, RegIII, RegIV, and EXTL3. Binding of EXTL3 to a Reg gene in the tumor cell is thus inhibited.

DETAILED DESCRIPTION OF THE INVENTION

One of the problems with functional genomics is the sheer mass of data that are accumulated. For example, one can identify many genes whose expression varies under certain pathological conditions, but such variation does not imply a causative role for the genes identified. Functional studies must be devised to determine whether a gene whose expression varies is a relevant gene in the pathological condition. The present inventors have found that the Reg family of genes (broadly defined to include both the Reg ligands and their receptors) plays an important and deleterious role in the neoplastic process. In particular, the Reg family has been found to be involved in resistance to apoptosis inducing agents including anti-cancer therapeutic agents, such as chemotherapeutic agents and radiation.

Since the Reg family plays a deleterious role in the health of the cancer patient, is expressed rarely or at significantly lower levels in normal tissues, and is an extracellular protein family, it is an excellent target for therapeutic intervention. The Reg family functions by binding to a cell surface receptor, thought to be EXTL3. Thus, antagonism of the binding reaction of the ligand and receptor, or antagonism of expression of either the ligand or receptor can provide a therapeutic modality.

In order to antagonize the binding of either the ligand or receptor, an antibody can be used. The term "antibody" as used herein includes both monoclonal and polyclonal antibodies, as well as antibody portions or derivatives that contain the variable region of an antibody. Such portions or derivatives include, but are not limited to, single chain Fv (ScFv), Fab, F(ab')$_2$, and Fv. Also included are conjugates that present the variable region on a framework of another molecule. The antibody specifically binds to a Reg family ligand or receptor, preferably binding far less to other unrelated proteins. The binding to a desired Reg family target and to other proteins preferably differs by at least a factor of $10^2$, $10^3$, $10^4$, $10^5$, or $10^6$. Antibodies have long been administered to humans for a variety of purposes. Any method of administration known in the art can be used in the context of the present invention, including but not limited to intravenous, intraperitoneal, subcutaneous, intramuscular, intranasal, intrabronchial, intratumoral, and per os administration.

Additionally non-steroidal anti-inflammatory drugs (NSAIDs) and COX-2 inhibitors in particular can be administered to the tumor cell. Such drugs include indomethacin, naproxen, ibuprofen, naproxen, aspirin, celecoxib, diclofenac, etodolac, fenoprofen, ketoprofen, ketoprofen, ketorolac, oxaprozin, nabumetone, sulindac, tolmetin, valdicoxib (Bextra®) and rofecoxib. These can be administered simultaneously with the antibodies or before or after, preferably within 1 day, 1 week, or 1 month of the antibodies.

Therapeutic radiation can also be administered to the same tumor cell (or if in a patient, to the same cancer patient). Similarly anti-cancer chemotherapeutic agents can be administered to the same tumor cell or cancer patient. Such agents include: x-rays, cisplatin (Platinol®), daunorubicin (Cerubidine®), doxorubicin (Adriamycin®), etoposide (VePesid®)), methotrexate (Abitrexate®), mercaptopurine (Purinethol®), fluorouracil (Adrucil®), hydroxyurea (Hydrea®), Vinblastine (Velban®), Vincristine (Oncovin®), Irinotecan (Camptosar®, CPT-11), Levamisole, selective epidermal growth factor receptor tyrosine kinase inhibitors (e.g. ZD1839, Iressa®) and Pacitaxel (Taxol®). Preferably the agents co-administered with the antibodies are ones that induce apoptosis.

The types of tumors and tumor cells that are good targets for the treatments of the present invention include those of the non-squamous gastrointestinal tract (e.g. esophageal, gastric, small intestine, colon and rectal adenocarcinomas), the hepatobiliary tract and the pancreas. Suitable tumor targets also include ovarian, brain, prostate, breast, germ cell tumors, papillary serous carcinoma, lung carcinoma, acute myelogenous leukemia, B-cell chronic lymphocytic leukemia, insulinoma, prostate adenocarcinoma, fibrosarcoma, juvenile granulosa tumor cells. Other tumor cells, especially those which express members of the Reg gene ligand and receptor family can be targeted.

Similar to the antibody-type therapeutic agents, antisense constructs, small interfering RNAs (siRNAs), antisense oligonucleotides, and RNA interference constructs can be used to increase apoptosis in cancer cells. These agents function by preventing or interfering with expression of the Reg gene family of ligands and receptor. The use of such agents is well known in the art.

Antisense constructs, antisense oligonucleotides, RNA interference constructs or siRNA duplex RNA molecules can be used to interfere with expression of any of the members of the Reg gene ligand and receptor family. Typically at least 15, 17, 19, or 21 nucleotides of the complement of the selected mRNA sequence are sufficient for an antisense molecule. Typically at least 19, 21, 22, or 23 nucleotides of the selected RNA are sufficient for an RNA interference molecule. Preferably an RNA interference molecule will have a 2 nucleotide 3' overhang. If the RNA interference molecule is expressed in a cell from a construct, for example from a hairpin molecule or from an inverted repeat of the desired Reg gene family sequence, then the endogenous cellular machinery will create the overhangs. siRNA molecules can be prepared by chemical synthesis, in vitro transcription, or digestion of long dsRNA by Rnase III or Dicer. These can be introduced into cells by transfection, electroporation, or other methods known in the art. See Hannon, G J, 2002, RNA Interference, *Nature* 418: 244-251; Bernstein E et al., 2002, The rest is silence. *RNA* 7: 1509-1521; Hutvagner G et al., RNAi: Nature abhors a double-strand. *Curr. Opin. Genetics & Development* 12: 225-232; Brummelkamp, 2002, A system for stable expression of short interfering RNAs in mammalian cells. *Science* 296: 550-553; Lee NS, Dohjima T, Bauer G, Li H, Li M-J, Ehsani A, Salvaterra P, and Rossi J. (2002). Expression of small interfering RNAs targeted against HIV-1 rev transcripts in human cells. *Nature Biotechnol.* 20:500-505; Miyagishi M, and Taira K. (2002). U6-promoter-driven siRNAs with four uridine 3' overhangs efficiently suppress targeted gene expression in mammalian cells. *Nature Biotechnol.* 20:497-500; Paddison P J, Caudy A A, Bernstein E, Hannon G J, and Conklin D S. (2002). Short hairpin RNAs (shRNAs) induce sequence-specific silencing in mammalian cells. *Genes & Dev.* 16:948-958; Paul C P, Good P D, Winer I, and Engelke D R. (2002). Effective expression of small interfering RNA in human cells. *Nature Biotechnol.* 20:505-508; Sui G, Soohoo C, Affar E-B, Gay F, Shi Y, Forrester W C, and Shi Y. (2002). A DNA vector-based RNAi technology to suppress gene expression in mammalian cells. *Proc. Natl. Acad. Sci. USA*

99(6):5515-5520; Yu J-Y, DeRuiter S L, and Turner D L. (2002). RNA interference by expression of short-interfering RNAs and hairpin RNAs in mammalian cells. *Proc. Natl. Acad. Sci. USA* 99(9):6047-6052.

Antisense or RNA interference can be delivered in vitro to tumor cells or in vivo to tumors in a mammal. Typical delivery means known in the art can be used. For example, delivery to a tumor can be accomplished by intratumoral injections. Other modes of delivery can be used without limitation, including: intravenous, intramuscular, intraperitoneal, intraarterial, subcutaneous, and per os. Conversely in a mouse model, the antisense or RNA interference can be administered to a tumor cell in vitro, and the tumor cell can be subsequently administered to a mouse. Vectors can be selected for the desirable properties for any particular application. Vectors can be viral or plasmid. Non-viral carriers such as liposomes or nanospheres can also be used.

Additional therapeutic agents or candidate therapeutic agents can be identified using a binding assay. The assay can be performed in vitro using purified proteins, or using whole cells. A Reg gene family ligand protein is contacted with EXTL3 protein, in the presence and absence of a test substance. The order of the contacting can be varied. All components can be, but need not be simultaneously contacted. Pairs of reagents can be pre-bound, for example, and displacement by a third reagent can be assessed. The test substances can be natural products or synthetic products; they can be single compounds or combinations of compounds. They can be known or unknown for another use. They can be pre-selected based on structural similarities to other compounds, or they can be screened randomly. Any binding assay known in the art can be used. A two-hybrid type assay can be used in which expression of a reporter gene is dependent on the binding of two binding partner proteins. Alternatively, one of the binding partners may be bound to a solid support. One binding partner can be labeled. Bound or unbound complexes can be separated from the assay mixture, for example, using immunoprecipitation. Another assay utilizes cells which express one of the binding partners on their cell surface and the other binding partner is added exogenously. Any format for assessing binding between two proteins can be used. Once a binding inhibitor of the Reg gene family ligand and receptor has been identified, it can be used therapeutically to treat tumor cells and tumors. The inhibitor can be administered by any route, particularly intravenous, intramuscularly, subcutaneously, and per os.

All cited references are expressly incorporated herein in their entireties for all purposes. While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

EXAMPLES

Example 1

Expression of Reg Genes in Humans

Figure 3:
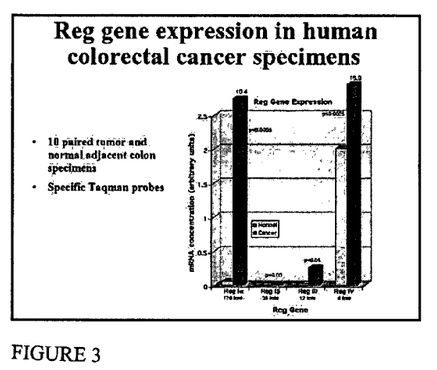
FIG. 3 shows Reg gene mRNA expression in human colorectal cancer specimens.
Figure 4:
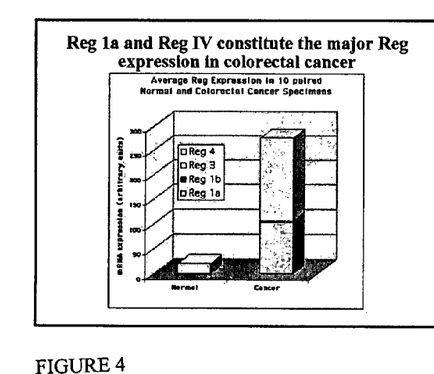
FIG. 4 shows Reg 1a and Reg IV constitute the major Reg expression in colorectal cancer.
Figure 5:
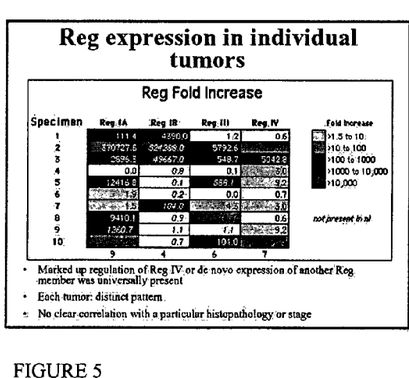
FIG. 5 shows Reg expression in individual tumors.

Reg gene expression was examined in 10 human colorectal adenocarcinoma specimens (FIGS. 3 and 4). Gene expression was measured using individual Reg-specific Taqman probe and primer sets in tumors and paired adjacent normal mucosa. FIG. 3 shows expression of the four individual human Reg mRNAs expressed as fold increase over expression in the normal colonic mucosa. Significant increases in the average Reg Iα, Reg Iβ, Reg III, and Reg IV were shown. FIG. 4 shows that Reg IV is the predominant Reg gene expressed in normal colonic mucosa. While tumorigenesis was accompanied by increases in all Reg genes, Reg Iα and Reg IV constitute the dominant Reg genes expressed in colorectal adenocarcinoma. FIG. 5 shows Reg expression (as a fold increase) in individual tumor specimens relative to the expression in the paired adjacent normal mucosa. Marked upregulation of Reg IV or de novo expression of another Reg member was universally present in each specimen. Each tumor demonstrated a unique mixture of Reg gene overexpression. 70%, 60%, 90%, and 40% of tumors show increases in Reg IV, Reg III, Reg Iα, and Reg Iβ greater than 1.5 fold over adjacent normal mucosa, respectively. No clear correlation with a particular histopathology or tumor stage was evident. In addition to expression in gastrointestinal malignancy, review of Unigene (Reg Iα, Hs.449407 (old number Hs.1032); Reg Iβ, Hs.4158; Reg III (PAP), Hs.423; Reg IV, Hs.105484) revealed expression in additional malignancies including germ cell tumors, papillary serous carcinoma, lung carcinoma, acute myelogenous leukemia, B-cell chronic lymphocytic leukemia, insulinoma, prostate adenocarcinoma, fibrosarcoma, juvenile granulose tumor.

Example 2

Expression of Reg Genes in Mouse

Figure 6:
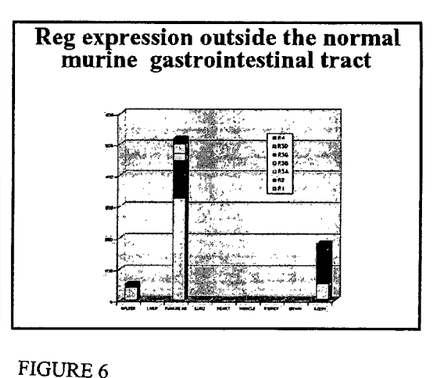
FIG. 6 shows Reg expression outside the normal murine gastrointestinal tract.
Figure 7:
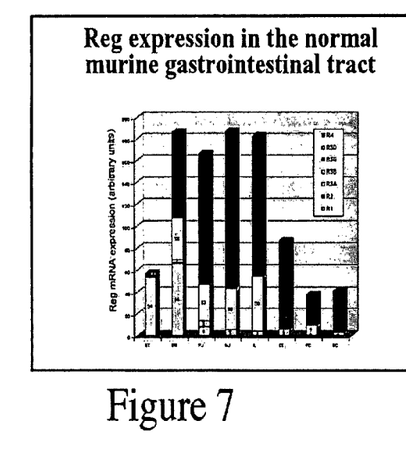
FIG. 7 shows Reg expression in the normal murine gastrointestinal tract.

Reg gene expression was characterized in the normal mouse to allow further study in well-defined murine tumorigenesis models (FIG. 6 and 7). Undetectable or low levels of the seven known murine Reg family members (listed in FIG. 1) were present in most non-gastrointestinal tissues. FIG. 6, showing tissues outside the luminal GI tract (with ileum as a reference on both FIGS. 6 and 7) reveals significant expression in the spleen and pancreas. The columnar gastrointestinal tract, shown in FIG. 7, in contrast, reveals distinct region-specific expression profiles for individual members of the murine gene family along the cranio-caudal axis (e.g. prominent Reg I expression in the proximal, Reg IIIγ and Reg IIIβ in the mid, and Reg IV in the distal gastrointestinal tract).

Figure 8:
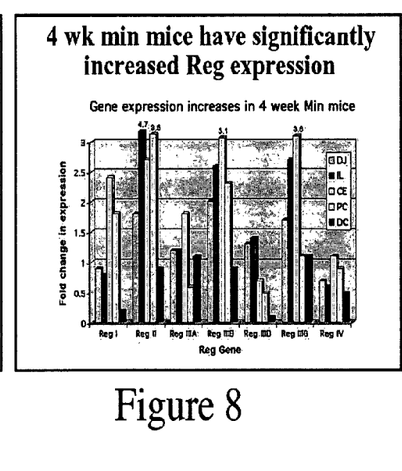
FIG. 8 shows that 4 week min mice have significantly increased Reg expression.
Figure 9:
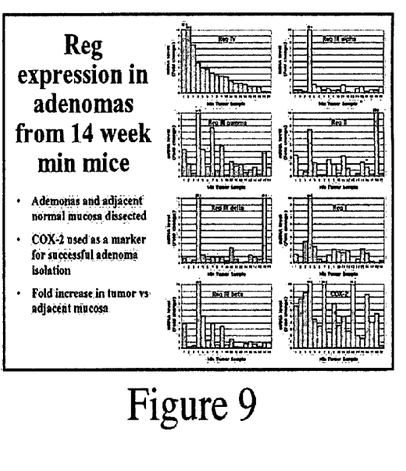
FIG. 9 shows Reg expression in adenomas from 14 week min mice.
Figure 10:
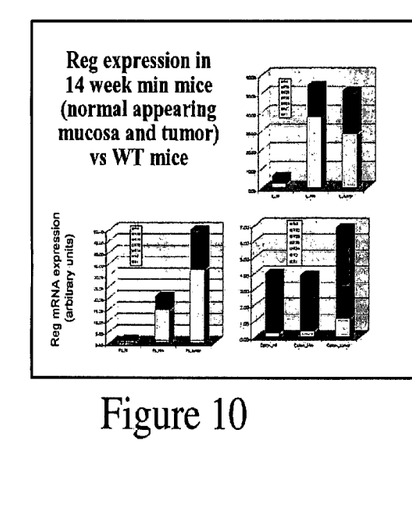
FIG. 10 shows Reg expression in 14 week min mice (normal appearing mucosa and tumor) versus wild-type mice.
Figure 12:
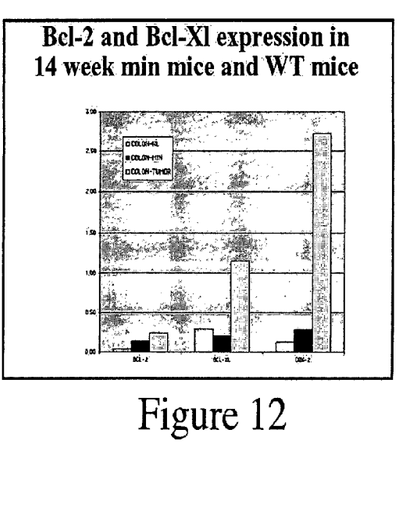
FIG. 12 shows Bcl-2 and Bcl-XI expression in 14 week min mice and wild-type mice.

The APC (min) murine genetic model [APC(min/+)] of human gastrointestinal malignancy was studied to determine when Reg gene expression becomes dysregulated during tumorigenesis. Mutation of both copies of the APC gene is an early event in human colorectal cancer. Four week old min mice are heterozygous for the wild type APC gene despite a morphologically normal appearing epithelium. Tumors develop after a second spontaneous mutation occurs in the remaining normal copy of the APC gene. FIG. 8 shows that four week old mice have significantly increased Reg expression (1=normal mucosa). These results suggest that increased Reg may act as a tumor promoter or play a causative role in determining the malignant phenotype. At 14 weeks, visible adenomas [genotype (min/min)] were dissected along with a paired sample from nearby normal appearing mucosa [genotype (min/+) or (min/min)]. FIG. 9 shows gene expression in individual min tumors. COX-2 overexpression was used as a marker for successful adenoma isolation (increased seen in all but sample 19). Reg IV was most commonly increased in tumors, yet like human colon cancer specimens, individual tumors displayed unique patterns of Reg gene expression. FIG. 10 shows the alterations in Reg gene expression resulting from a APC (min) gene dose effect. This figure compares (A) normal litermate controls [APC (+/+)], (B) normal appearing 14 week mucosa [APC (min/+) or (min/min)], and (C) gross adenomas [APC (min/min)] in the proximal jejunum (PJ), ileum (IL), and colon. Increased expression for individual Reg genes occurred progressively in a region-specific fashion. FIG. 12 shows that this APC gene dosage effect was seen with the expression of anti-apoptotic genes Bcl-2, Bcl-xl, and COX-2. Patients with familial adenomatous polyposis (FAP), characterized by mutation in the APC gene also show significant upregulation of Reg IV (our data, not shown). These results collectively suggest that the APC min mouse is a valid model for the study of human colorectal malignancy.

Example 3

Correlation of Reg IV and Bcl-2 Expression

Figure 11:
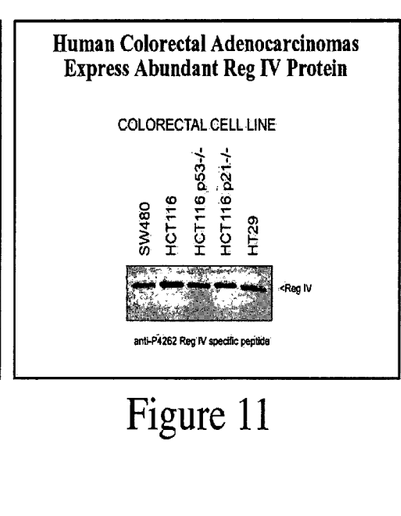
FIG. 11 shows that human colorectal adenocarcinomas express abundant Reg IV protein.
Figure 13:
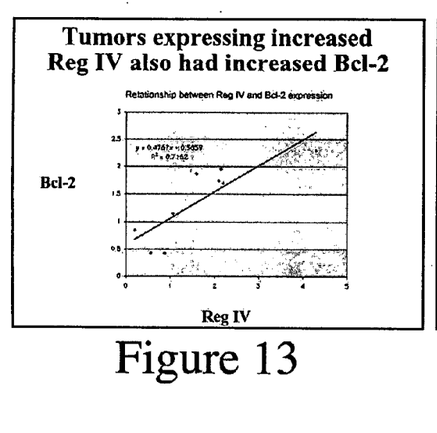
FIG. 13 shows that tumors expressing increased Reg IV also had increased Bcl-2.

FIG. 11 shows that human colorectal adenocarcinomas express abundant Reg IV protein, paralleling increases described above for Reg IV mRNA. This expression was demonstrated by Western blot using monospecific anti-Reg IV antibody (also see FIG. 22). The possible relationship between increased Reg IV and increases in Bcl-2 mRNA. FIG. 13 shows that tumors specimens with increases in Reg IV mRNA (as a fold change compared with normal adjacent mucosa) also had increased levels of Bcl-2 mRNA. This data shows a close correlation between Reg IV overexpression and tumor expression of Bcl-2, an antiapoptotic protein.

Example 4

Functional Relationship Between Reg and Bcl Genes

Figure 14:
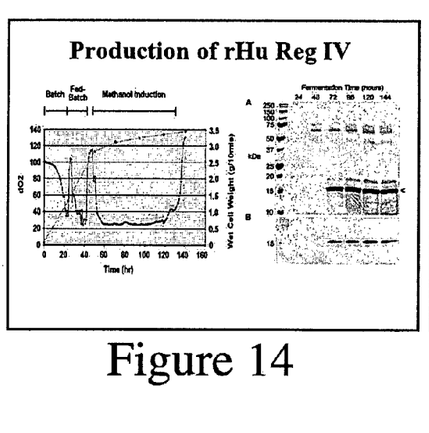
FIG. 14 shows production of recombinant human Reg IV.

To determine if the relationship between increased Reg IV and antiapoptotic gene expression was causative or simply correlative, we expressed recombinant Reg Iα, Reg III, and Reg IV by fermentation in *Pichia pastoris*. Details of the recombinant human Reg IV protein production and purification are outlined in Example 11 and FIG. 14. Reg Iα and Reg III were expressed and purified in the same manner using methanol induction, centrifugation, sequential applications of tangential flow filtration/ultrafiltration followed by preparative HPLC. FIG. 14 (left) shows results of the fermentation of *Pichia pastoris* expressing recombinant human Reg IV using an optimized fed-batch protocol. Plotted parameters show the dissolved oxygen concentration (dO2, ♦) and wet cell weight (□) during 144 hours of culture. The initial batch phase growth occurred in media containing 40 g/liter glycerol. Following a marked rise in dO2 occurring as a result of carbon source limitation at around 26 hrs, the glycerol fed-batch process was initiated. Glycerol was provided at 40 mls/hr for 14 hours to induce rapid expansion of the *Pichia* cell mass. Production phase was initiated by methanol feeding after a 3 hr carbon-source starvation. The rate of methanol feeding was slowly ramped up over 8 hours as described in methods and continued until 134 hours.

FIG. 14 (right) shows the analysis of recombinant human Reg IV by SDS-PAGE. Clarified culture supernatants were sampled at various times during the fermentation run and analyzed by Coomassie blue stained gels. Samples taken at approximately 24 and 48 hrs were during growth on glycerol, and at 72, 96, 120, and 144 hrs were after activation of the alcohol oxidase (AOXJ) promotor by methanol induction. Arrows indicate bands corresponding to the expected size of human Reg IV at 15.6 kDa. Western blot of a duplicate gel after immunostaining with 2H6, a monoclonal raised against recombinant human Reg IV. Bands were visualized by enhanced chemiluminescence (ECL, Amersham).

Figure 15:
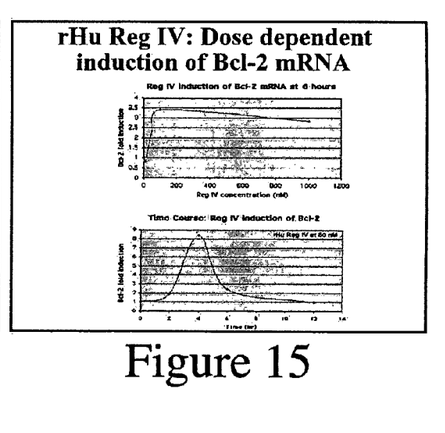
FIG. 15 shows dose-dependent induction of Bcl-2 mRNA by recombinant human Reg IV.
Figure 16:
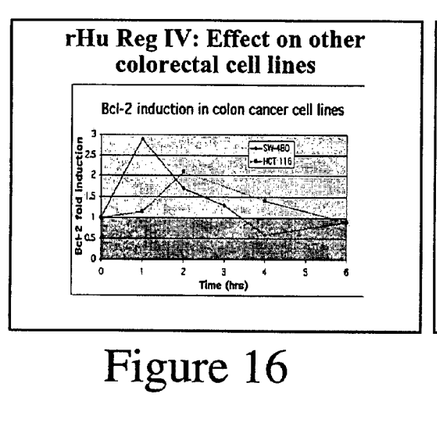
FIG. 16 shows the effect on other colorectal cell lines of recombinant human Reg IV.
Figure 18:
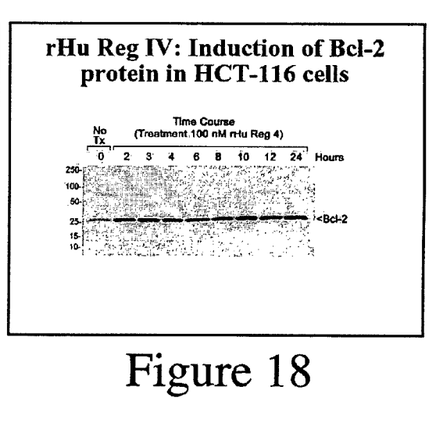
FIG. 18 shows induction of Bcl-2 protein in HCT-116 cells by recombinant human Reg IV.
Figure 29:
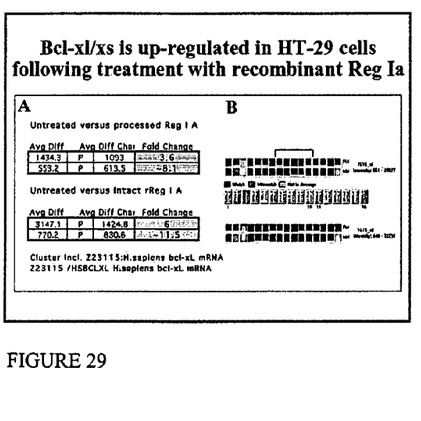
FIG. 29 shows that Bcl-xl/xs is upregulated in HT-29 cells following treatment with recombinant human Reg Ia.
Figure 30:
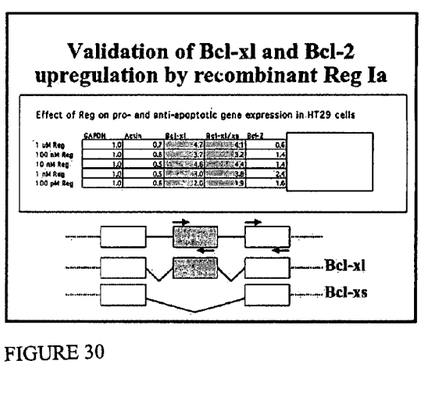
FIG. 30 shows validation of Bcl-xl and Bcl-2 upregulation by recombinant Reg Ia.

FIG. 15 shows that treatment with recombinant Reg IV results in a dose-dependent induction of Bcl-2 in HT29 colon cancer cells. Additional colorectal cell lines were also examined to determine if this was a generalized effect on gastrointestinal cells. Bcl-2 induction also followed treatment with Reg IV in SW480 and HCT116 cells. To determine if the increases in Bcl-2 mRNA also were associated with changes in Bcl-2 protein expression, Western blotting was performed on cell lysates taken at various times following Reg treatment. FIG. 18 shows that by 2 hours after Reg IV treatment, Bcl-2 is significantly upregulated at a protein level. FIG. 29 and 30 show that recombinant Reg Iα results in increased expression of Bcl-xl and Bcl-2. These results suggest that exogenous Reg proteins causally regulate the expression of anti-apoptotic genes. These results are particularly impressive given the endogenous production of Reg proteins occurring in gastrointestinal malignancy and further demonstrates the utility of therapeutic strategies designed to interrupt Reg signaling in gastrointestinal malignancy.

Figure 17:
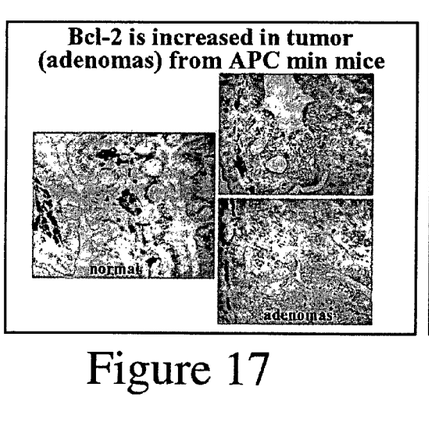
FIG. 17 shows that Bcl-2 is increased in tumor (adenomas) from APC min mice.

Increased expression of Bcl-2 in tumor adenomas provides additional support for the role of increased antiapoptotic proteins in tumor behavior. FIG. 17 shows immunohistochemistry using anti-Bcl-2 antibody on normal and adenoma tissues. Although not easily appreciated in this black and white picture, Bcl-2 expression in the normal intestine is restricted to the immune cell population in the lamina propria. In tumor sections, diffuse cytoplasmic staining is appreciated throughout the adenoma epithelium.

Example 5

Functional Relationship Between Akt and Reg IV

Figure 19:
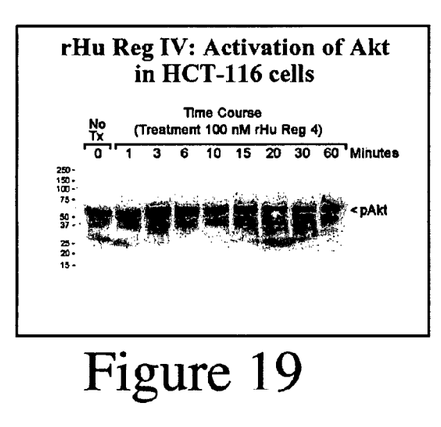
FIG. 19 shows activation of Akt in HCT-116 cells by recombinant human Reg IV.
Figure 20:
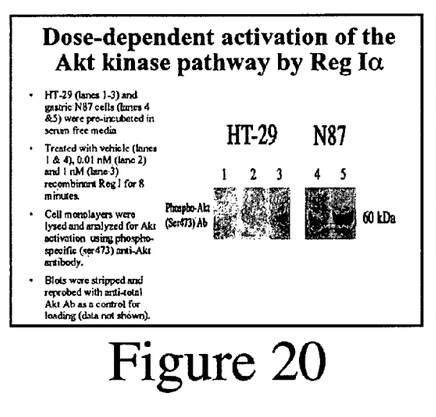
FIG. 20 shows dose-dependent activation of the Akt kinase pathway by Reg Iα.

One kinase responsible for protection against apoptosis in tumor cells may be Akt/protein kinase B. Akt, also referred to as Rac, regulates the balance between survival and apoptosis by several mechanisms. Akt may regulate the expression of anti-apoptotic proteins. Because of the effect of Reg on the regulation of Bcl-2 (and Bcl-xl, discussed later), we examined the effects of recombinant Reg IV and Reg Iα on the activation of the Akt pathway. FIGS. 19 and 20 show that nanomolar concentrations of recombinant Reg results in rapid activation by phosphorylation of Akt in colon cancer cell lines (HCT116, HT29) and gastric cancer cells (N87). These data support the role of Reg proteins in the activation of the Akt pathway in gastrointestinal malignancies. Activated Akt has known pleiotropic effects (beyond effects on Bcl-2 family gene expression), reducing the amount of apoptosis occurring either at baseline or in response to a known proapoptotic stimulus. Thus our results suggest that interruption of the downstream effects of Reg proteins (e.g., upregulation of anti-apoptotic gene expression and activation of Akt) would increase tumor cell death at baseline or in response to therapies that result in enhanced apoptotic cellular death (e.g., radiation and chemotherapeutic agents).

Example 6

Immunohisotchemical Localization of Reg IV Expression

Figure 23:
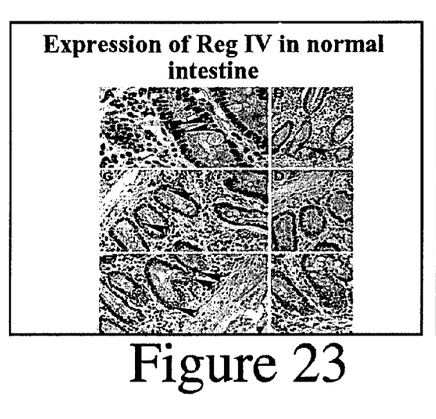
FIG. 23 shows expression of Reg IV in normal intestine.
Figure 24:
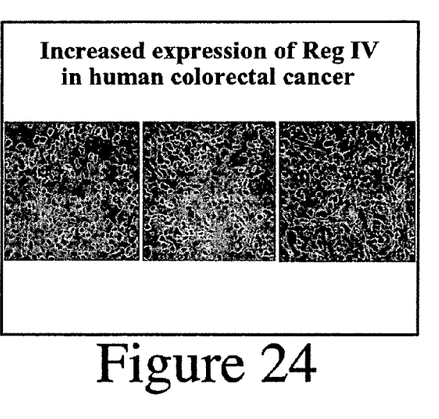
FIG. 24 shows increased expression of Reg IV in human colorectal cancer.

Expression of Reg IV in the normal intestine and upregulation of epithelial expression in colorectal malignancy are shown in FIGS. 23 and 24. FIG. 23 shows the identification of Reg IV protein expression in the normal gastrointestinal mucosa. Paraffin embedded sections of normal human ileum were subjected to immunohistochemical analysis using the TSA-indirect tyramide immunostaining kit (NEN Life Science, Boston, Mass.). The 2H6 anti-human Reg IV monoclonal antibody (A, B, C) reacted with the 1-2 epithelial cells per crypt. Immunoreactive cells were typically located 2-10 cell positions from the base of the crypt (arrowhead). Rabbit polyclonal anti-P4261 (E, F). Anti-P4262 showed identical staining patterns (not shown). FIG. 24 shows epithelial staining from 3 sections of colorectal carcinoma.

Figure 22:
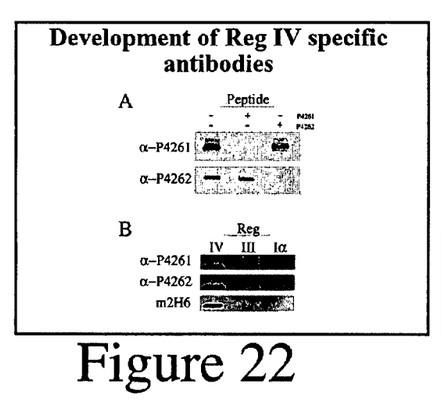
FIG. 22 shows the development of Reg IV specific antibodies.

Development of monospecific monoclonal and polyclonal antibodies to Reg IV are described in example 3 and shown in FIG. 22. FIG. 22 details the immunologic studies showing (22A) identification of recombinant human Reg IV with affinity-purified Rabbit anti-peptide antibodies, and (22B) specificity of individual antibodies for Reg IV by Western blot. In panel A, rabbit antibodies at 2 µg/µl were preincubated for 1 hour in blocking buffer alone, or in blocking buffer containing either 0.1 µg/µl of peptide P4261 or P4262 before use in Western Blot. In panel B, specificity of the two individual rabbit anti-peptide antibodies and 2H6, a hamster anti-human Reg IV monoclonal antibody, were determined by Western blot using ~0.5 µg of recombinant human Reg IV, Reg III, or Reg Iα.

Example 7

Function of Reg Proteins

Figure 21:
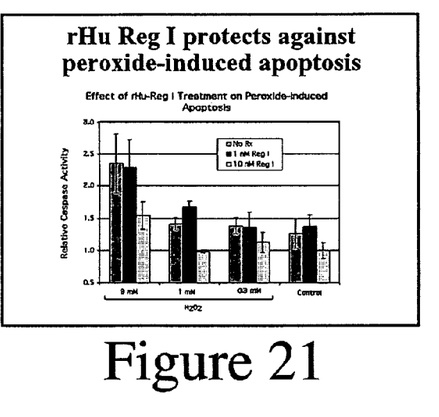
FIG. 21 shows that recombinant human Reg IV protects against peroxide-induced apoptosis.

FIG. 21 shows that nanomolar concentrations of recombinant Reg Iα result in reduced caspase activity in HT29 lysates following an oxidative stress (treatment with hydrogen peroxide).

Example 8

Reg Exression Response to Irradiation

Figure 25:
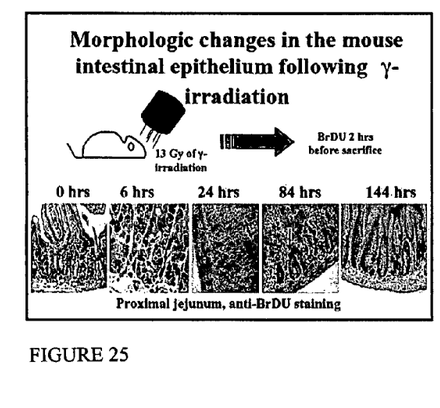
FIG. 25 shows morphologic changes in the mouse intestinal epithelium following γ-irradiation.
Figure 26:
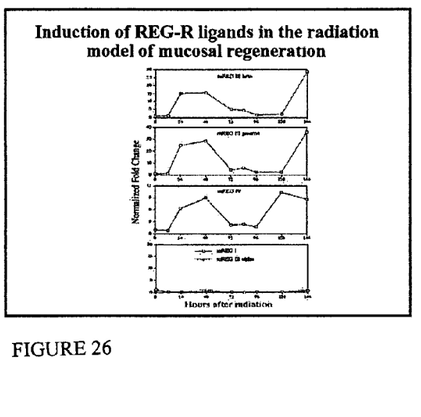
FIG. 26 shows induction of Reg-R ligands in the radiation model of mucosal regeneration.

Gamma irradiation is a well-defined pro-apoptotic stimulus and is a commonly applied experimental approach to study intestinal epithelial cell death. FIG. 25 shows the morphologic changes that occur at specific times in the intestine in response to gamma irradiation. At 6 hours marked apoptosis is seen in the crypt epithelium. By 24 hours, there is a loss of epithelial proliferation. Regenerating crypts, counted at 84 hours, are reflective of a single surviving stem cell. By 144 hours the intestinal epithelium shows restoration of the normal architecture. FIG. 26 shows that radiation results in upregulation of endogenous Reg gene expression in the intestine.

Example 8

Functional Effect of Reg Proteins on Intestinal Stem Cells and Cancer Cells

Figure 27:
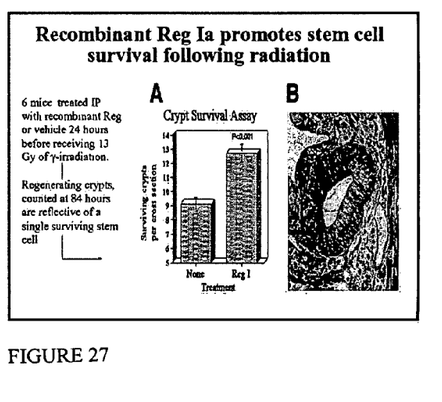
FIG. 27 shows that recombinant Reg Ia promotes stem cell survival following radiation.
Figure 28:
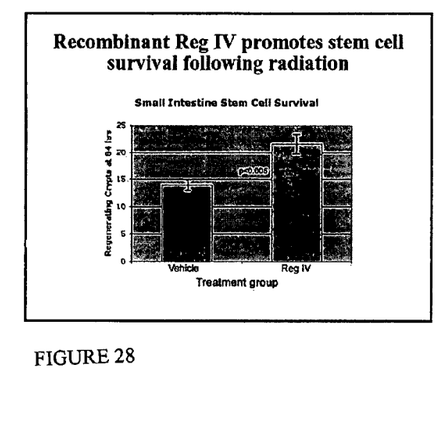
FIG. 28 shows that recombinant human Reg IV promotes stem cell survival following radiation.
Figure 31:
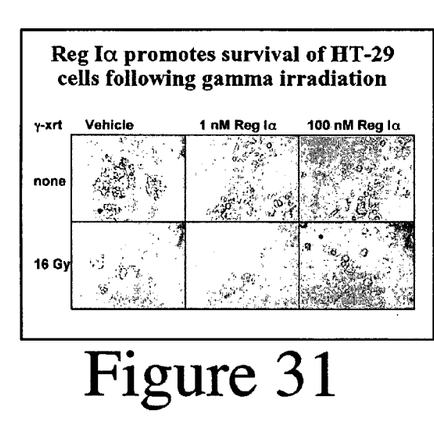
FIG. 31 shows that Reg Ia promotes survival of HT-29 cells following gamma irradiation.
Figure 32:
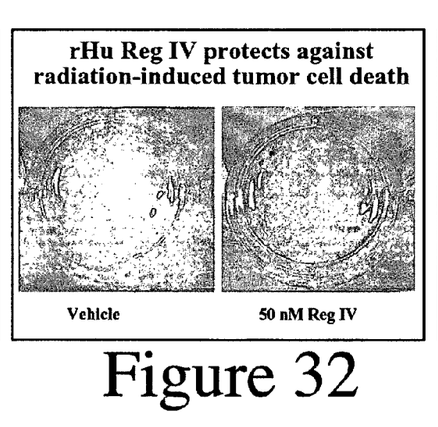
FIG. 32 shows that recombinant human Reg IV protects against radiation-induced tumor cell death.

Stem cells and their immediate progeny are the only cells in the normal epithelium that are capable of continued proliferation. In this context, epithelial malignancies may reflect a form of disordered stem cell biology. FIGS. 27 and 28 show the effect of exogenous Reg proteins on the survival of intestinal stem cells following 13 Gy radiation. Pretreatment with recombinant Reg Iα and Reg IV lead to significantly increased stem cell survival. The results suggest that the multiple anti-apoptotic effects of Reg proteins provide functional protection from a well-defined pro-apoptotic stimuli in normal epithelium. Reg expression is upregulated in gastrointestinal cancer, where current literature supports a functional resistance to apoptotic stimuli. We therefore conducted experiments to see if exogenous Reg would promote the survival of colorectal adenocarcinoma cells in response to gamma radiation. These results (shown in FIGS. 31 and 32) show that nanomolar concentrations of Reg Iα and Reg IV lead to improved cell survival from gamma radiation.

Example 9

Reg Gene Family Coördinate Autoregulation

Figure 33:
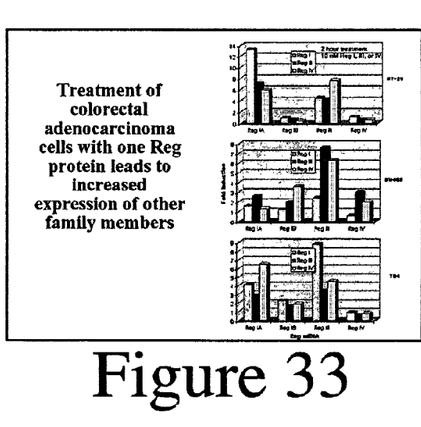
FIG. 33 shows that treatment of colorectal adenocarcinoma cells with one Reg protein leads to increased expression of other family members.

Our results above suggest that a number of the functional properties of Reg IV are also shared by Reg Iα, the most dissimilar member of the family (nucleotide/protein sequence similarity). One explanation for this finding could be that a single Reg protein can upregulate expression of other members of the Reg family. FIG. 33 shows that treatment of a number of colon cancer cell lines (e.g. HT29, SW480, T84) with recombinant Reg proteins (e.g. Reg Iα, Reg III, and Reg IV) leads to the upregulation of mRNA coding for other members of the Reg gene family. These results suggest that one should focus on the collective gene family in the design of a therapeutic to disrupt Reg signaling in malignancy.

Example 10

Isolation of a Reg receptor

A cell surface receptor has been identified for Reg I. We isolated a ~110 kDa cell surface protein present on two rat cell lines which were mitogenically stimulated by recombinant Reg I. A cell surface receptor for rat pancreatic stone protein of ~110 kDa was isolated using interaction cloning ($^{125}$I-labeled Reg I used to probe an islet xZAP II cDNA expression library) (Kobayashi S., et al. JBC 275:10723-26, 2000). The encoded rat protein sequence was >97% identical to a previously cloned human gene, EXT-like gene 3 (EXTL3), also known as EXT related gene 1 (EXTR1). EXTL3 is a member of a new gene family that is highly conserved from *Caenorhabditis elegans* to higher organisms. The idea that this molecule may be a Reg receptor is unexpected since this gene family was not thought to contain cell surface receptors or to have a role in cell surface signaling. Our data support that EXTL3 is the Reg receptor since we isolated it by Reg-specific affinity chromatography.

The first 332 amino acids of EXTL3 contain the Reg I recognition domain (the portion of the molecule represented in the original cDNA clone, Kobayashi et al.) By peptide phage display, we have also demonstrated that Reg is predicted to interact with a short peptide sequence represented in the amino terminal portion of the molecule. No data are available concerning receptor binding by other members of the Reg gene family (i.e., Reg Iβ, Reg III and Reg IV). A search using the standard BLAST algorithm has not revealed any additional genes with significant homology to this predicted Reg I binding domain. Furthermore, this domain seems to be uniquely present in EXTL3, but not in the other members of the exostoses family. Characterization of rat EXTL3 shows it to be a 919 amino acid protein, predictive of a type II transmembrane protein with a short intracellular domain (residues 1-28), a transmembrane domain (residues 29-51), and a long extracellular domain (residues 52-919). The intracellular domain of this molecule lacks known signaling motifs that would be expected for a functional receptor. This suggests that this molecule may not be the complete Reg signaling complex.

Example 11

Production, Purification, and Characterization of Recombinant Reg IV

We recently identified Reg IV, a novel regenerating gene product that is uniquely expressed by the normal distal gastrointestinal mucosa. The function remains poorly understood due to the lack of significant purified Reg IV for biochemical and functional studies. Recombinant human Reg IV was efficiently expressed under the control of the AOX1 gene promoter in *Pichia pastoris* using the Mut$^S$ strain KM71H. We describe the unique conditions that are required for efficient production of Reg IV protein in high density fermentation. Optimal protein expression was obtained by reduction of the fermentation temperature and addition of casamino acids as a supplemental nitrogen source and to minimize the activity of yeast produced proteases. Recombinant Reg IV protein was purified by tangential flow filtration and reverse phase chromatography. The purified protein was characterized by amino terminus sequence analysis and MALDI-TOFMS showing that the engineered protein had the expected sequence and molecular weight without secondary modification. Recombinant Reg IV was further characterized by specific monoclonal and polyclonal reagents that function for Western Blot analysis and for immunolocalization studies.

Materials and Methods

Vectors, Strains and Supplies: The pPICZα vector (Invitrogen) was used to direct secretion of human Reg IV. The pGEM-T Easy vector (Promega) was used to clone and sequence the PCR product. *Escherichia coli* DH5α was used for subcloning and Reg IV-pPICZα vector cloning. The *Pichia pastoris* strain KM71H (genotype, arg4 aox1::ARG4) was used for Reg IV protein expression. Preparative-scale (Pellicon 2) Biomax polyethersulfone cartridges with an 8 kDa and 50 kDa molecular weight cutoff and Durapore cartridges with a 0.45 μM pore size were purchased from Millipore. Antifoam 204 (Sigma) was autoclaved and used at a 1:50 dilution. Components of the trace mineral solution [Fe$_2$(SO$_4$)-7H$_2$O, 65 gm/liter; ZnSO$_4$, 42.2 gm/liter; CuSO$_4$-5H$_2$O, 6 gm/liter; MnSO$_4$-H$_2$O, 3 gm/liter; CoCl$_2$-6H$_2$O, 0.5 gm/liter; Na$_2$MoO$_4$-2H$_2$O, 0.2 gm/liter; NaI, 0.08 gm/liter; H$_3$BO$_3$, 0.02 gm/liter] were purchased from Sigma.

Construction of the human regenerating gene IV expression vector: The cloning and cDNA sequence for human Reg IV has been previously reported. The cDNA encoding the mature secreted form of Reg IV, lacking the signal sequence, was amplified by PCR using the specific primers 5'-GGAATTCGATATCATCATGAGACCCAGCTG-3' (SEQ ID NO: 7) and 5'-CTAACTCCTGCACAGCCCCGTCCTCTAGAGG-3' (SEQ ID NO: 8). The forward primer contained an EcoR I site for cloning into pPICZα. The reverse primer incorporated the native stop codon and an engineered Xba I site. PCR products and vector were digested with EcoR I and Xba I, gel purified and ligated together. *E. ccli* DH5α was chemically transformed with the recombinant vector and cultured at 37° C. on low-salt LB with Zeocin (25 μg/ml) for selection of recombinants. The recombinant plasmid hReg IV-pPICZα was sequenced to ensure 100% identity with the expected nucleotide sequence and in-frame orientation.

Construction and Isolation of Reg IV expressing *P. pastoris* clones: The hReg IV-pPICZα plasmid was purified and linearized with Sal I prior to electroporation into *P. pastoris* KM71H. Yeast transformants were selected on YPD agar plates (2% Bacto peptone, 1% yeast extract, 2% dextrose) containing 1M sorbitol and 100 μg/ml Zeocin. Individual Zeocin resistant clones were screened for protein production in 50 ml culture tubes. Colonies were used to innoculate 5 mls of BMGY media and grown with shaking overnight. Subsequently the yeast were collected by centrifugation and resuspended in ¼$^{th}$ of the original culture volume of BMMY media. Fresh methanol was added to 0.5% every 24 hours and cells were cultured for a total of 72 hours at 30° C. with shaking. Cleared supernatants were screened for protein expression by 12% SDS-PAGE and Coomassie brilliant blue R250 staining. Reg IV expressing *Pichia* clones were suspended in YPD media with 15% glycerol and stored at −80° C. Limited quantities of recombinant Reg IV were produced by direct scale up of these conditions in 2 liter shaker flasks.

Fermentation: Fermentation of the hReg IV (Mut$^s$) transformant of *P. pastoris* was carried out using a BioFlo 110 fermenter (New Brunswick Scientific Co.) equipped with software control (BioCommand Plus) of temperature (26 and 30° C.), agitation (1000 rpm), pH, anti-foam addition, supplemental oxygen addition (dO$_2$≧30% and ≧25%) and data logging. A frozen stock of KM71H containing the expression construct Reg IV-pPICZα was used to inoculate a 2 liter baffled flask containing 300 mls of YNB-glycerol media. After overnight incubation, the shaker flask contents were transferred to the 5.6 liter working volume fermenter containing 3.5 liters of fermentation basal salt-glycerol media [H$_3$PO$_4$, 27 ml/liter; CaSO$_4$-2H$_2$O, 0.9 gm/liter; K$_2$SO$_4$, 18 gm/liter; MgSO$_4$-7H$_2$O, 15 gm/liter; KOH, 4.1 gm/liter; glycerol 40 gm/liter; D-biotin, 0.87 mg/liter] supplemented with 4.4 ml/liter trace mineral solution. pH was maintained at 5.0 with 28% (w/v) NH$_4$OH during batch and fed-batch growth on glycerol. Growth in batch mode was continued until the dissolved oxygen concentration increased as a result of carbon source limitation (26 hours). A 50% glycerol feeding solution was initiated (40 mL/hour) for 14 hours and supplemental oxygen automatically administered to maintain the dissolved oxygen concentration above 30%. After 3-4 hour carbon source starvation, methanol feeding was initiated (100% methanol containing 12 ml trace minerals/liter) at 4 ml/hour for 2 hours, and the feed rate then increased by 2.7 mls every 2 hours to a final rate of 12 mu hour. At the initiation of the 96 hour production phase, and again after 24 hours, 10 grams of casamino acids (DIFCO laboratories) were added as a supplemental nitrogen source and to minimize the activity of yeast produced proteases. During the production phase, the temperature of the reaction chamber was reduced to 26° C. and supplemental oxygen was added as needed to maintain the dO$_2$≧25%. Similar protocols were applied to the production and purification of Reg Iα and Reg III.

Protein Purification and Analysis: Fermentation broth containing the secreted rHuReg IV protein was collected by centrifugation (3500 rpm). The supernatant was processed in a Millipore Pellicon-2 tangential flow filtration apparatus using a PVDF Durapore membrane with a pore size of 0.45 μM. The filtrate was retained and processed through a Biomax 50K polyethersulfone membrane. This filtrate was then processed through a Biomax 8K polyethersulfone membrane. The final purification step involved preparative reverse phase HPLC of the 8K retentate solution [Biomolecules Midwest (Waterloo, Ill.)]. Samples were eluted using a gradient of trifluoracetic acid, acetonitrile. Selected fractions were analyzed by Matrix Assisted Laser Desorption Ionization Time-of-Flight Mass Spectrometry (MALDI-TOFMS) on an Applied Biosystems Voyager-DE STR instrument (Foster City, Calif.). Additional samples were subjected to SDS-PAGE. Proteins were transferred to PVDF membrane and Coomassie stained. Individual bands were excised and subjected to Edman N-terminal sequence analysis on a PE-Biosystems Procise ABI494 (Foster City, Calif.).

Generation of polyclonal anti-Reg IV antibodies. Rabbit polyclonal anti-Reg IV specific antibodies were produced by immunization with KLH-coupled synthetic peptides. Synthetic peptides, RSWSGKSMGGNKHC (corresponding to residues 94-107), with a native C-terminal Cysteine and TIAEYISGYQRSQPC (residues 56-69), containing a non-native C-terminal Cysteine were synthesized by Biomolecules Midwest (Waterloo, Ill.) and coupled to maleimide-KLH (Pierce). Polyclonal antisera were produced by Harlan Bioproducts (Indianapolis, Ind.) using their standard rabbit protocol. Antibody titer was determined in a microtiter plate ELISA using Reg IV as the immobilized antigen. Immunoglobulins were affinity purified by peptide-sulfolink resin (Pierce). Final antibody concentrations were determined by BCA Assay (Pierce).

Monoclonal antibody production, ELISA, and Western Blot analysis: Armenian hamster monoclonal antibodies were produced to rHuReg IV at the hybridoma center at Washington University using standard protocols (e.g., URL address: http file type, domain name pathbox.wustl.edu, directory ~hcenter). Briefly, a primary subcutaneous immunization was given using 100 micrograms of recombinant human Reg IV in Complete Freunds Adjuvant. Repeat SC booster immunizations were given at days 16 and 31 using incomplete Freunds Adjuvant, followed by a final IV boost given 4 weeks later. Splenocytes were fused to the P3X63Ag8.653 murine myeloma line 3 days after the IV boost using 50% w/v PEG 1500 and were plated under HAT selection. Supernatants were collected 14 days after fusion and hybridoma clones secreting antibodies specific for Reg IV were identified by ELISA using goat anti-Armenian hamster IgG coupled to horseradish peroxidase (Jackson ImmunoResearch, West Grove, Pa.) followed by colorimetric detection (TMB substrate, Pierce Corp., Rockford, Ill.). Positive clones were subcloned a second time to insure clonality. Positive and negative controls included a 1:100 dilution of serum collected from the immunized Armenian hamster and supernatants from several unrelated hybridoma cultures. Specificity of individual clones was further examined by duplicating the ELISA experiments using plates coated with rHuReg Iα and Reg III. Immunoglobulin from Reg IV-specific hybridoma cultures was isolated using ImmunoPure IgG purification system (Pierce) and the final antibody concentration was determined using the BCA Assay (Pierce). Monoclonal and polyclonal specificity and suitability for use in Western blot analysis were further examined. Five hundred nanograms of recombinant human Reg IV, Reg III, and Reg Iα were subjected to SDS-PAGE electrophoresis in 10-20% gradient gels (BioRad, Hercules, Calif.) and transferred to PVDF membranes. Membranes were blocked and incubated with 0.1 micrograms/ml of IgG from individual hybridoma clones or polyclonal serum. Goat anti-Armenian hamster IgG or goat anti-rabbit IgG coupled to horseradish peroxidase (Jackson labs) was applied as a secondary antibody and immunoreactivity visualized by ECL (Amersham).

Tissue Immunohistochemistry: Formalin fixed paraffin embedded sections of normal human ileum were prepared using standard techniques and were subjected to immunohistochemical analysis. Slides are first treated with a solution of Antigen Decloaker for the monoclonal antibody or Nuclear Decloaker for the polyclonal antibodies (Biocare Medical, Walnut Creek, Calif.) in a pressure cooker @ 15 PSI for 3 minutes. Monoclonal and polyclonal antibodies were initially tested over a range of dilutions in a commercial blocking solution (Protein Block, Dako, Carpenteria, Calif.). Optimal staining with the polyclonal antibodies was between 1:2000 and 1:4000 (0.75-1.5 micrograms/ml), and at 1:100 (0.7 micrograms/ml) with the monoclonal antibody. Sections were stained using the TSA-Indirect immunohistochemistry kit (NEN Life Science, Boston, Mass.). Appropriate biotinylated anti-rabbit or anti-hamster IgG secondary antibodies (NEN Life Science, Boston Mass.) at a dilution of 1:2000, were prepared and applied according to the NEN protocol. Controls consisted of staining without the addition of primary antibody or the use of polyclonal antibodies in the presence of excess synthetic peptides. For blocking experiments, antibodies were preincubated with synthetic peptides at a concentration of 100 micrograms/ml for 1 hour at room temperature before incubation with the tissue section. Positive staining was visualized using the HRP chromogenic substrate 3,3'-diaminobenzidine (Vector Laboratories, Burlingame, Calif.) followed by a light hematoxylin counterstain.

Results

Expression of recombinant human Regenerating gene IV in *P. pastoris*. The cDNA corresponding to mature human Reg IV was fused in frame with the *Saccharomyces cerevisiae* α-mating factor secretion signal in the vector pPICZα (Invitrogen Corporation, Carlsbad, Calif.). This construct provides antibiotic selection in both *E. coli* and *P. pastoris* and directs the synthesis and extracellular secretion of Reg IV coupled with cleavage of the amino-terminal secretion sequence. This fusion protein is placed under the control of the *Pichia* AOX1 methanol-inducible promoter. As a result of our cloning strategy, two additional amino acids, Glu-Phe, follow the second Ste13 cleavage site, and precede the Asp-Ile-Ile-Met residues that initiate the amino terminus of mature Reg IV. Structural homology between Glu-Ala, a known Ste13 site, and Glu-Phe, raised the possibility that Ste13 might also recognize this as an alternative cleavage site. Approximately 300 Zeocin resistant transformants of KM71H resulted from electroporation, which were of the expected Mut$^S$ phenotype. Twenty-five were randomly selected and screened for functional expression of the Reg IV protein by SDS-PAGE and Coomassie staining. At selected intervals following methanol induction, aliquots of the cleared culture supernatant were examined to identify the clone with the highest level of Reg IV protein production.

Fermentation and characterization of recombinant hReg IV in *P. pastoris*. The *P. pastoris* expression clone selected above was used for production of human Reg IV in shaker flask culture (*Pichia* Manual, Invitrogen Corporation, Carlsbad, Calif.). Yields of protein were approximately 1-2 mg per liter of starting culture, disappointingly low for planned animal studies. Accordingly, we attempted to scale up production in both yield and volume by fermentation. Fermentation of the clone expressing hReg IV was carried out using a BioFlo 110 fermenter (New Brunswick Scientific Co.) equipped with software control of the growth conditions and data logging. An overnight broth of KM71H containing the expression construct hReg IV-pPICZα was used to inoculate 3.5 liters of fermentation basal salt-glycerol media in a 5.6 liter working volume fermenter. The initial batch phase growth occurred in media containing 40 gm/liter glycerol (FIG. 14, left). Following a marked rise in dO2 occurring as a result of carbon source limitation at approximately 26 hrs, the glycerol fed-batch process was initiated. Glycerol was provided as a 50% glycerol solution containing 12 ml/liter of the trace minerals solution, administered at 40 mls/hr for 14 hours to induce rapid expansion of the *Pichia* cell mass (FIG. 14). The production phase was initiated by methanol feeding after a 3 hr carbon-source starvation. The rate of methanol feeding was slowly ramped up over 8 hours and continued until 134 hours. The software control was set to maintain dO2≧30% during growth on glycerol and ≧25% during growth on methanol, requiring administration of supplemental oxygen between 28-42 hrs and between 58-103 hrs. Although not a part of a regular production batch, in some runs the methanol feeding was discontinued at 134 hours to assess the time until depletion of the carbon source, by dO2 monitoring. Typically, the dO2 would rise to ≧100% within 2-3 hrs (FIG. 14). At the initiation of the 96 hour production phase, and again after 24 hours, 10 grams of casamino acids were added as a supplemental nitrogen source and to minimize the activity of yeast produced proteases. During the production phase, the temperature of the reaction chamber was reduced to 26° C. Fermentation runs performed without a reduction in the reaction chamber temperature or without the addition of casamino acids had appreciably less of the Reg IV product running at ~15-16 kDa in association with the prominent appearance of lower molecular weight proteins of approximately 8 and 12 kDa molecular weight by SDS-PAGE. Amino terminus sequencing of these lower bands revealed the expected N-terminus of Reg IV, demonstrating that these lower molecular weight bands resulted from internal proteolysis near the carboxy terminus.

The production of recombinant human Reg IV was monitored by SDS-PAGE and Coomassie blue staining (FIG. 14, right). Samples taken at approximately 24 and 48 hrs, during growth on glycerol, lacked significant expression of any secreted protein. Whereas samples taken at 72, 96, 120, and 144 hrs, all times following activation of the alcohol oxidase (AOX1) promoter, had a prominent band at ~15 kDa, corresponding to the expected size of human Reg IV. To determine the identity of this band, Western blotting was performed using the monoclonal and two polyclonal antibodies generated as described in methods. FIG. 14, right "B" shows a duplicate gel after immunostaining with 2H6, a monoclonal raised against recombinant human Reg IV. Bands were visualized by enhanced chemiluminescence (ECL, Amersham). Identical staining was demonstrated using anti-P4262 and anti-P4261, polyclonal antibodies raised against 15-mer synthetic peptides representing two non-overlapping sequences derived from the human Reg IV cDNA sequence.

Purification steps. Recombinant human Reg IV was initially purified by tangential flow filtration. As is typical for the methylotrophic yeast *Pichia pastoris*, cleared supernatants are pale green in color. The centrifuged fermentation supernatant (~3500 ml) was initially cleared using a 0.1 square meter Durapore 0.45 μM PVDF cartridge. Proteins or protein aggregates greater than 50 kDa were discarded in the Biomax 50 kDa polyethersulfone cartridge retentate. The substance resulting in the green color of the media was also removed in this step. A 50 kDa cutoff was selected because of the paucity of protein contaminants below this mass, and the well described propensity for other Reg family members to undergo dimerization. Seventy percent of the Reg IV was recovered in the 50 kDa permeate. Contaminants less than 8 kDa were then removed in the discarded 8 kDa permeate. Overall, thirty-five percent of the original Reg IV was recovered in the 8 kDa retentate (~250 mls). Higher yields could be obtained by greater flushing of the 50 and 8 kDa filter cassettes, but this comes at the price of a significantly larger dilution of the final protein solution. The final purification step involved preparative $C_{18}$RP-HPLC. Differences in the retention time as well as the broad elution profile for the fermentation sample suggested that there could be differences in the final protein products. Individual bands were subjected to Edman N-terminal sequence analysis on a PE-Biosystems Procise ABI494 (Foster City, Calif.). Unexpectedly, the processing and secretion of Reg IV differed between shaker flask production and fermentation. Furthermore, the leading shoulder for each preparation contained a prominent higher molecular weight band in addition to the expected Reg IV product. Edman N-terminal sequence of Reg IV produced by batch growth in a shaker flask was the DIIMRPSC (SEQ ID NO: 9), the expected amino terminus of mature Reg IV. The higher molecular weight band gave an identical sequence suggesting that this is a dimeric species of Reg IV that has survived both $C_{18}$RP-HPLC and heat treatment at 95 degrees C. for 5 minutes in the presence of SDS and DTT prior to SDS-PAGE analysis. The N-terminal sequence of Reg IV produced under fermentation conditions was EFDIIMRPSC (SEQ ID NO: 5), reflecting inclusion of the two additional amino acids, Glu-Phe, that follow the second Ste13 cleavage site. A similar dimeric species containing the extended N-terminus was observed for the fermentation sample, yet tended to "bleed-across" the entire peak unlike the shaker flask counterpart. This data highlights the potential for differences in the processing and secretion of recombinant Reg IV unique to specific Pichia growth conditions. MALDI-TOFMS of the Reg IV produced by batch growth in a shaker flask showed a $MW_{expt.}$ of 15,917.3 in good agreement with an expected unmodified $MW_{calc.}$ of 15,913.9. MALDI-TOFMS for Reg IV produced by fermentation showed a $MW_{expt.}$ of 16,192.7, in agreement with a $MW_{calc.}$ of 16,190.2, corresponding to the amino terminus starting with EFDIIMR (SEQ ID NO: 6).

Immunologic characterization of the recombinant Reg IV protein. We elected to proceed with the development of Reg IV isoform specific antibodies by two independent methods; monoclonal antibodies and unique synthetic peptide-derived polyclonal antibodies. The identification of recombinant human Reg IV with affinity-purified Rabbit anti-peptide antibodies is shown in FIG. 22. Both anti-P4261 and anti-P4262 specifically detected the recombinant protein and both could be blocked in the presence of the specific peptide used for immunization. The specificity of each individual antibody for Reg IV by Western blot is shown in FIG. 22. All three antibodies specifically recognized Reg IV and failed to react with recombinant human Reg Iα or Reg III.

These specific antibodies provided the first opportunity to investigate the tissue and cellular localization of Reg IV. Paraffin embedded sections of normal human ileum were subjected to immunohistochemical analysis (FIG. 23). The 2H6 anti-human Reg IV monoclonal antibody (FIG. 23A, B) strongly reacted with the 1-2 individual epithelial cells per crypt. Immunoreactive cells were typically located 2-10 cell positions from the base of the crypt (arrowhead). High powered views showed that positive crypt cells appeared to be enterocytes by morphology and were not Paneth cells (by DIC microscopy) or enteroendocrine cells (by a Fontana-Masson argentaffin staining reaction, data not shown). Scattered cells also showed positive staining higher in the crypt or on the villus surface. These cells had a different morphology, resembling enteroendocrine cells. In serial sections these cells were found to be positive by Fontana-Masson argentaffin staining. Negative controls included sections stained, with omission of the primary antibody (FIG. 23D), or stained with an unrelated antibody (not shown). To provide independent validation, rabbit polyclonal anti-P4261 and anti-P4262 staining was perfomed. These experiments demonstrated an identical staining pattern. Controls for the rabbit polyclonal antibodies included staining in the presence of the competing synthetic peptide used for immunization.

Example 4

Tissues with significant (>30 tags/million) expression of Reg genes by SAGE analysis are listed below for each Reg gene.

Hs.9018: exostoses (multiple)-like 3 (A putative Reg receptor)

Ovarian Clear cell carcinoma cell line ES-2, poorly differentiated (31)
Brain, Duke glioblastoma multiforme cell line, Duke_H392 (86)
Brain, Duke glioblastoma multiforme primary tumor derived from a 51 year old male, GBM_H1110 (112)
Brain, 5 pooled Duke glioblastoma multiforme primary tumors, pooled_GBM (47)
Glioblastoma multiforme, Duke_H247_normal (32)
Brain, normal, greater than 95% white matter. Post-mortem delay of 3:15, BB542 (41)
Brain, normal human astrocyte cells harvested at passage 5, NHA(5th) (37)
Brain, normal, pooled, normal_pool(6th) (47)
Ovarian Clear cell carcinoma cell line ES-2, poorly differentiated, ES2-1 (31)
Prostate cancer cell line, LNCaP (127)

Primary ovarian tumor, serous adenocarcinoma, OVT-6 (46)
Primary tumor, serous adenocarcinoma, OVT-7 (36)
Hs.49407 (Old Number Hs. 1032): Reg Ia, Regenerating islet-derived 1 alpha (pancreatic stone protein, pancreatic thread protein)
Prostate cancer cell line, LNCaP (31)
Human breast adenocarcinoma from a malignant pleural effusion, SK-BR-3 (119)
Colon, primary tumor, Tu102 (103)
Colon, primary tumor, Tu98 (100)
Hs.423: Reg III, pancreatitis-associated protein, PAP
Colon, primary tumor, Tu102 (103)
Hs.4158: Reg Ib, Regenerating islet-derived 1 beta (pancreatic stone protein, pancreatic thread protein)
Colon, primary tumor, Tu102 (34)
Hs.105484: Reg IV, Regenerating gene IV, gastrointestinal secretory protein GISP

We claim:

1. A method of treating a colorectal cancer, comprising:

delivering to colorectal tumor cells which express a human Reg IV protein an antibody which specifically binds to a human Reg IV protein as set forth in SEQ ID NO: 4, in an amount sufficient to inhibit the Reg IV protein's anti-apoptotic effect on the tumor cells.

2. A method comprising:

delivering to colorectal tumor cells an antibody which specifically binds to a human Reg IV protein as set forth in SEQ ID NO: 4, in an amount effective to increase death of the tumor cells.

3. A method comprising:

delivering to colorectal tumor cells an antibody which specifically binds to a human Reg IV protein as shown in SEQ ID NO: 4, in an amount effective to inhibit Bcl-2 up-regulation by Reg IV in the tumor cells.

4. The method of claim 1, 2, or 3 wherein the delivering comprises delivering the antibody by intravenous, intramuscular, or subcutaneous injection.

5. The method of claim 1, 2, or 3 wherein the tumor cells are selected from the group consisting of colon cells and rectal cells.

6. The method of claim 1, 2, or 3 wherein the tumor cells are colon tumor cells.

7. The method of claim 1, 2, or 3 wherein the tumor cells are rectal tumor cells.

8. The method of claim 1, 2, or 3 further comprising administering an NSAID.

9. The method of claim 1, 2, or 3 further comprising administering a COX-2 inhibitor.

10. The method of claim 1, 2, or 3 further comprising administering a chemotherapeutic drug.

11. The method of claim 1, 2, or 3 further comprising administering radiation.

* * * * *